United States Patent [19]

Wilcox et al.

[11] Patent Number: 5,743,436

[45] Date of Patent: Apr. 28, 1998

[54] APPLICATOR FOR DISPENSING MATERIAL FROM A DUAL CHAMBER CARTRIDGE

[75] Inventors: Malcolm W. Wilcox, Woodbury; Thomas W. Martin, Little Canada; Roger J. Carufel, Marine on St. Croix, all of Minn.

[73] Assignee: Minnesota Mining & Manufacturing Co., St. Paul, Minn.

[21] Appl. No.: 569,647

[22] Filed: Dec. 8, 1995

[51] Int. Cl.$^6$ ............................................ B67D 5/52
[52] U.S. Cl. .................... 222/137; 222/145.6; 222/327; 222/459; 433/90
[58] Field of Search ................ 222/137, 145.6, 222/327, 459; 433/89, 90

[56] References Cited

U.S. PATENT DOCUMENTS

| | | | |
|---|---|---|---|
| 4,121,739 | 10/1978 | Devaney et al. | 222/137 |
| 4,295,828 | 10/1981 | Rudler | 433/90 |
| 4,340,367 | 7/1982 | Vadas et al. | 433/89 |
| 4,366,919 | 1/1983 | Anderson | 222/137 |
| 4,431,414 | 2/1984 | Lawrence | 433/90 |
| 4,471,888 | 9/1984 | Herb et al. | 222/137 |
| 4,472,141 | 9/1984 | Dragan | 433/90 |
| 4,538,920 | 9/1985 | Drake | 366/177 |
| 4,801,008 | 1/1989 | Rich | 206/219 |
| 4,913,553 | 4/1990 | Falco | 366/129 |
| 5,005,735 | 4/1991 | Keller | 222/137 |
| 5,064,098 | 11/1991 | Hutter, III et al. | 222/137 |
| 5,080,493 | 1/1992 | McKown et al. | 366/177 |
| 5,082,147 | 1/1992 | Jacobs | 222/137 |
| 5,100,320 | 3/1992 | Martin et al. | 433/90 |
| 5,125,836 | 6/1992 | Dragan et al. | 433/90 |
| 5,129,825 | 7/1992 | Discko, Jr. | 433/90 |
| 5,137,181 | 8/1992 | Keller | 222/134 |
| 5,297,698 | 3/1994 | Martin | 222/95 |
| 5,306,147 | 4/1994 | Dragan et al. | 433/90 |
| 5,333,760 | 8/1994 | Simmen | 222/137 |
| 5,336,014 | 8/1994 | Keller | 403/24 |

FOREIGN PATENT DOCUMENTS

| | | | |
|---|---|---|---|
| 0161955 | 7/1988 | Japan | 433/90 |
| 9500078 | 1/1995 | WIPO | 433/90 |
| WO 95/22941 | 8/1995 | WIPO . | |

*Primary Examiner*—Joseph Kaufman
*Attorney, Agent, or Firm*—James D. Christoff

[57] ABSTRACT

A dispensing applicator includes a body with a handle, a pivotable lever and a front holder with a receptacle that is adapted to removably receive a dual chamber cartridge. In certain embodiments, the majority of the cartridge contents are expelled during a single stroke of the lever, an advantage when used for single patient use in dental or medical fields. In other embodiments, the holder is rotatably connected to the body so that the holder and the cartridge can be moved as needed in an arc in order to vary the orientation of the cartridge relative to the applicator handle. The rotatable connection enables the cartridge to be moved to any one of a number of different orientations as may be desired to provide optimum maneuverability of the applicator in use and to enhance the operator's vision of the application site.

10 Claims, 2 Drawing Sheets

APPLICATOR FOR DISPENSING MATERIAL FROM A DUAL CHAMBER CARTRIDGE

BACKGROUND OF THE INVENTION

1. Field of the Invention

This invention relates to an applicator for dispensing material made of two or more components from a dual chamber cartridge.

2. Description of the Related Art

A number of systems have been developed which are intended to serve as a shipping, storage, mixing and dispensing system for material made of two or more components. The systems often include an applicator and a replaceable cartridge that is detachably received in a receptacle of the applicator. The applicator typically includes a pair of linked-together plungers that dispense portions of each component simultaneously from the cartridge so that measuring of the separate components is unnecessary.

An example of a dual chamber dispensing system is described in U.S. Pat. No. 4,538,920 which is assigned to the assignee of the present invention. That system includes a cartridge with an exit conduit having a plurality of helical static mixing elements. During dispensing, the components are thoroughly mixed when passing through the exit conduit such that mixing by hand can be avoided.

Dual chamber dispensing systems such as that shown in U.S. Pat. No. 4,538,920 are widely used for dispensing a variety of materials used in industrial, commercial and residential settings. Examples of such materials include adhesives (such as epoxies), sealants, coatings and the like. The cartridge often holds a catalyst component in a first chamber and a base component in a second chamber that is isolated from the first chamber, so that the catalyst component does not react with the base component until such time as the applicator is operated to eject the components from the chambers and pass the components through the static mixer.

Dual chamber dispensing systems are also widely used in dentistry for storing, mixing and dispensing impression material. Often, the impression material is dispensed into an impression tray before the tray is placed in the oral cavity. Occasionally, however, the dental practitioner may attempt to use the system to deliver impressioning material directly into the oral cavity, as for example when an impression of only a single tooth is needed. Unfortunately, conventional dual chamber cartridge dispensing systems are somewhat bulky and hinder placing the material in certain areas of the oral cavity, particularly in posterior areas where access is limited.

Moreover, there has been increased interest in recent years in the field of dentistry for relatively small dual chamber dispensing systems that are especially useful for single-patient applications. Such single-use systems may be used, for example, for dispensing two-component materials that serve as an adhesive, base, liner, luting agent, sealant or filling material for restorative or endodontic use. A relatively small dispensing system is a particular advantage when used with dental restorative materials because the smaller size enables the practitioner to more easily dispense the material directly to a selected site within the oral cavity and to do so with better visibility of the application site.

Published PCT application no. PCT/US95/02411 (also assigned to the assignee of the present invention) describes a dental dispensing system wherein chambers of a dual chamber cartridge are located in an over-under orientation relative to the user's grip on the applicator, in contrast to conventional applicators wherein the chambers lie in a horizontally side-by-side orientation. The over-under orientation is especially useful for placing material in posterior regions of the patient's oral cavity that are difficult to access. The over-under orientation is also an advantage when used with patients that experience difficulty in opening their jaws to a relatively wide orientation.

While the dispensing system described in the foregoing PCT application no. PCT/US95/02411 is an advantage in many instances, there are certain situations where other orientations of the cartridge chambers relative to the applicator's handle might be desired to enhance maneuverability of the applicator and cartridge in use or improve the operator's visibility of the dispensing operation. However, the particular orientation of the cartridge as preferred by one practitioner may not be the same as a particular orientation of the cartridge as preferred by another practitioner. Furthermore, even a single practitioner may find it desirable from time to time to hold the cartridge in a somewhat different orientation than it was previously held in order to facilitate dispensing in certain instances.

SUMMARY OF THE INVENTION

The present invention concerns in one aspect an improved applicator for dispensing material from a dual chamber cartridge. The applicator comprises a body having a handle and a holder for removably receiving a dual chamber cartridge. The applicator also includes a pair of elongated, side-by-side plungers and drive means for advancing the pair of plungers in a certain direction toward the cartridge when received in the holder. The pair of plungers are pivotally connected to the body for selective movement in an arc about the aforementioned certain direction. The holder includes means for pivotally connecting the cartridge to the body for selective movement also in the arc in order to vary the rotative orientation of the cartridge relative to the handle.

The holder and the pair of plungers are preferably movable to a large number of different rotative orientations and more preferably are movable to an infinite number of different rotative orientations. As a consequence, the user can select an orientation that provides optimum maneuverability of the applicator and visibility of the dispensing operation when the applicator is in use. Both right-handed and left-handed operators can select the orientation which is least likely to cause operator fatigue and which will also provide the best results for the impending dispensing operation.

Another aspect of the present invention is directed toward an applicator assembly that comprises an applicator including a body having a handle, a lever pivotally connected to the body, and a pair of plungers shiftably coupled to the body. The lever is connected to the plungers for advancing the plungers relative to the body when the lever is moved a certain distance from a first location and to a second location relative to the handle. The applicator also includes a receptacle. The assembly also comprises a cartridge that is removably received in the receptacle and that has a pair of side-by-side chambers. The cartridge includes a pair of pistons received in the chambers and movable in the chambers over a limited path of travel. The plungers are in contact with the pistons for advancing the pistons when the lever is moved the certain distance. The chambers are of a size sufficiently small such that the pistons are moved a distance greater than one-half of their limited path of travel when the lever is moved the aforementioned certain distance such that at least one-half of the contents of the chambers is displaced from the chambers.

The present invention is also directed toward a dispensing method that comprises the step of placing a dual chamber cartridge in a receptacle of an applicator, wherein the cartridge includes an exit conduit having a static mixer and the cartridge chambers each contain a component of a multi-component material to be dispensed. The method also comprises the step of moving a lever of the applicator a certain distance in a single stroke in order to advance a pair of plungers of the applicator and move a pair of cartridge pistons a distance greater than one-half of their path of travel, such that at least a majority of the components are expelled from the chambers for passage through the exit conduit.

DETAILED DESCRIPTION OF THE PREFERRED EMBODIMENTS

Figure 1:
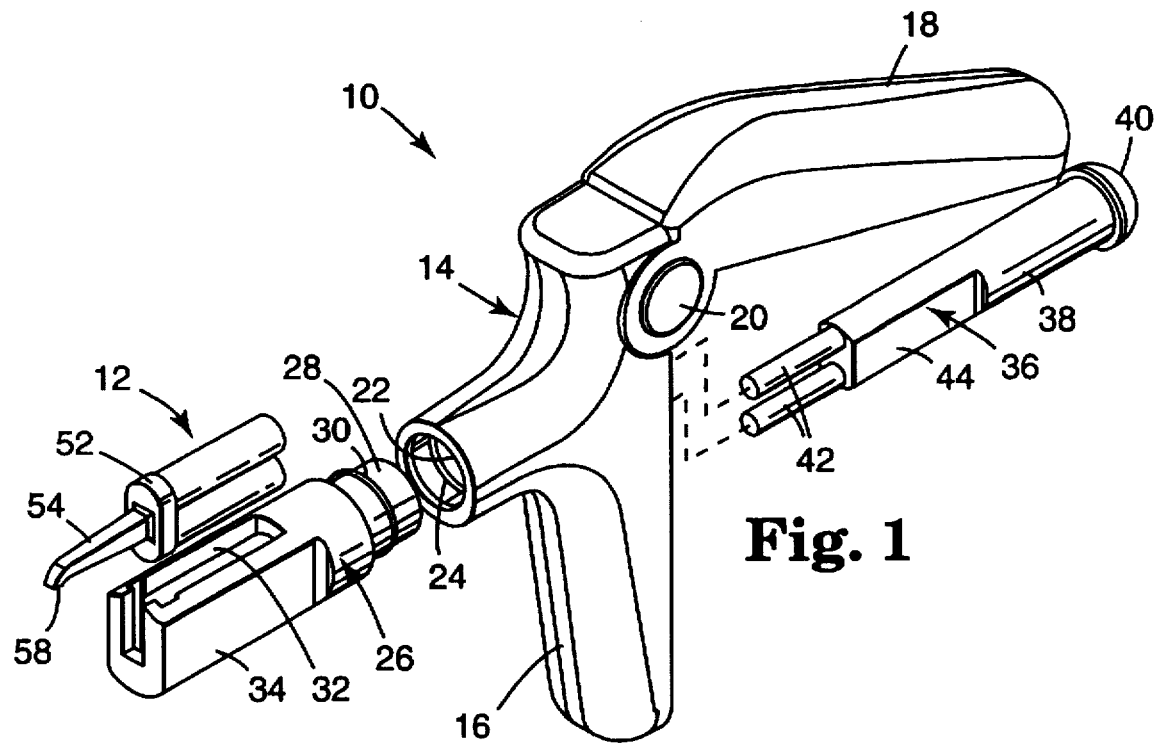
FIG. 1 is a top, front and right side exploded perspective view of an applicator constructed in accordance with the principles of the present invention.
Figure 2:
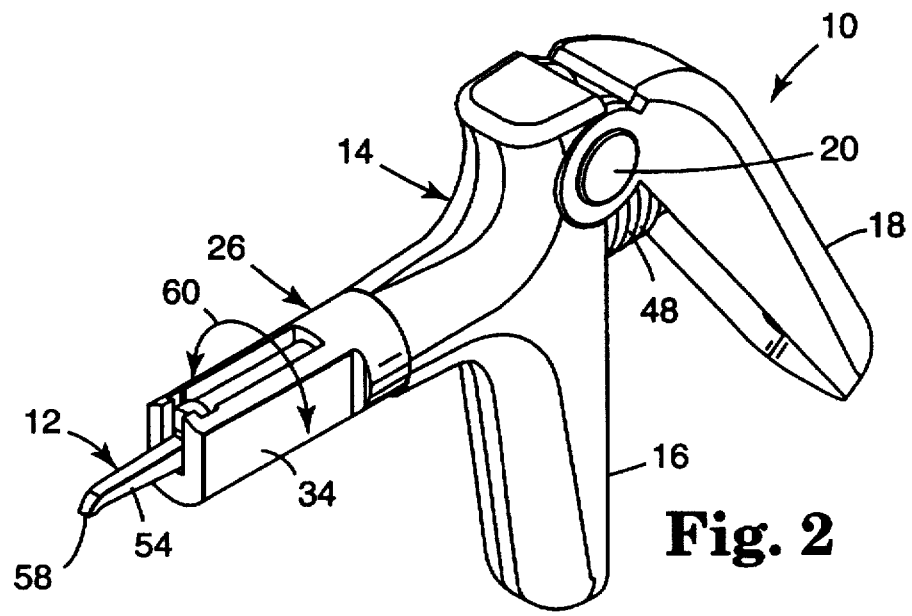
FIG. 2 is a non-exploded view somewhat similar to FIG. 1 except that a lever of the applicator has been advanced in readiness for a dispensing operation.
Figure 3:
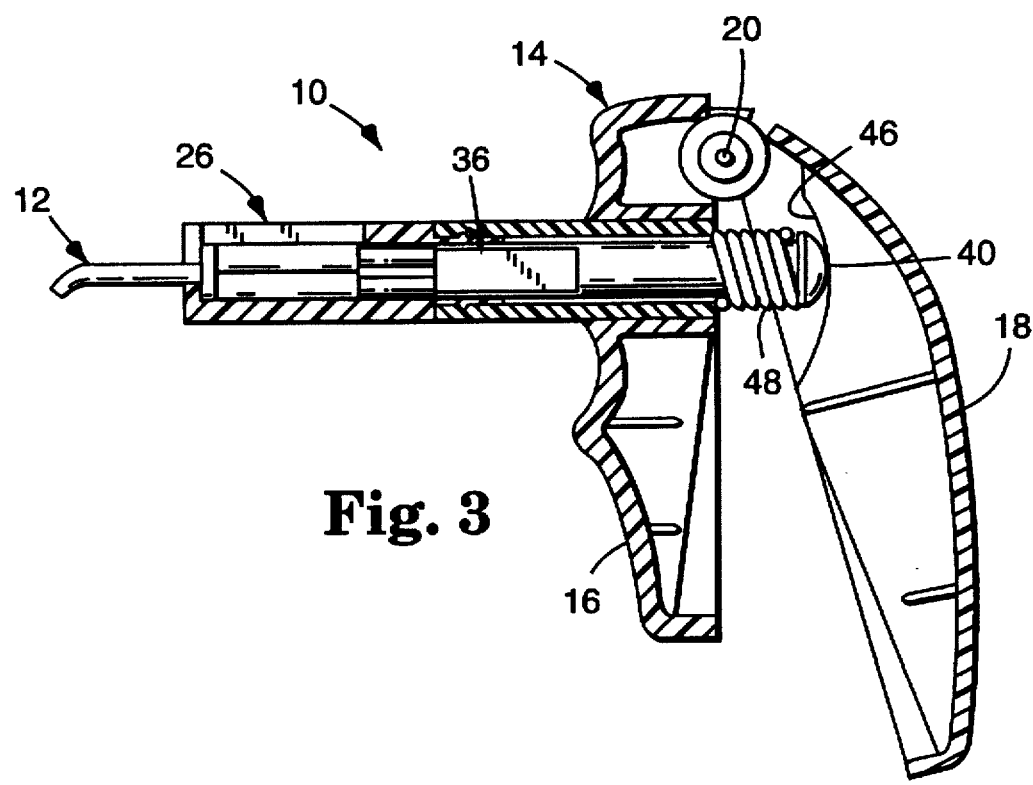
FIG. 3 is a side cross-sectional view of the applicator and cartridge illustrated in FIG. 2 except that the lever has been fully advanced to a position as it might appear after dispensing has been completed.

An applicator for dispensing material made of two or more components is designated broadly by the numeral 10 in FIGS. 1–3. The applicator 10 is adapted to dispense the components from a dual chamber cartridge 12 that is illustrated in combination with the applicator 10 in FIGS. 1–3. The cartridge 12 is also shown alone in FIG. 4.

The applicator 10 includes a body 14 with a depending handle 16. A rear lever 18 is connected to the body 14 by a pivot pin 20 for swinging movement about a horizontal reference axis when the handle 16 extends in a vertical direction.

The front of the body 14 includes a tubular projection having an internal cylindrical channel 22 (FIG. 1). The cylindrical wall of the channel 22 is interrupted by a circumscribing groove 24. The channel 22 is open on both ends and extends through an upper portion of the handle 16.

A cartridge holder 26 includes a cylindrical rear extension 28 (FIG. 1) that is matingly received in the channel 22. The extension 28 includes a raised circumferentially extending rib 30 that is received in the groove 24 when the extension 28 is fully inserted into the channel 22. Preferably, the rib 30 is received in the groove 24 in "snap-fit" relation with sufficient force to retain the holder 26 in coupled relation to the body 14 during ordinary use once assembled by the manufacturer.

The cartridge holder 26 includes an internal passage. A front section of the passage defines a receptacle 32 (FIG. 1) for removably receiving the cartridge 12. The holder 26 includes an opening next to the receptacle for insertion or removal of the cartridge 12 as well as a front slot to accommodate passage of a front nozzle or static mixer exit conduit of the cartridge 12 whenever the cartridge 12 is inserted or removed from the receptacle 32. Preferably, the shape of the receptacle 32 is complemental to the overall configuration of the cartridge 12 for snug reception of the latter although other configurations are, of course, possible.

The cartridge holder 26 also includes two flat sides, one of which is designated by the numeral 34 in FIGS. 1 and 2. The flat sides 34 enhance the operator's grip on the holder 26 for movement of the same when desired. In addition, the flat sides 34 reduce the bulk of the applicator 10 and improve visibility of the dispensing operation, a particular advantage when the operator's visibility to the application site is somewhat limited.

The body 14, the lever 18, the pivot pin 20 and the cartridge holder 26 are preferably made of a rigid, autoclavable synthetic resinous material. A suitable material is "RADEL" brand polyphenylsulfone, no. R5100, from Amoco.

The applicator 10 also includes a plunger device 36 that has an elongated shaft 38 with a rear, somewhat semispherical enlarged head 40. A pair of elongated, side-by-side cylindrical plungers 42 are connected to a front end of the shaft 38. Preferably, the plunger device 36 is integrally made of a relatively strong, wear-resistant, autoclavable material. As an example, the plunger device 36 may be integrally made of metal such as type 416 stainless steel, or made of a plastic body with stainless steel plungers connected to the body.

The plunger device 36 is slidably received in the channel 22 and is preferably connected to the holder 26 by keying structure so that the holder 26 and the plunger device 36 rotate simultaneously when the holder 26 is turned about its longitudinal axis. In the embodiment shown in the drawings, a pair of flat side walls 44 (one of which is depicted in FIG. 1) are located on opposite sides of the plunger device 36, and the side walls 44 are in abutting contact with mating, flat side walls located in a rear section of the internal passage of the holder 26. The keying structure enables the plunger device 36 to slide within the passage relative to the holder 26 when desired, but also insures that the holder 26 will turn simultaneously with turning movement of the plunger device 36 when moved in an arc about its longitudinal axis.

A drive means of the applicator 10 includes a pair of curved cam surfaces 46, one of which is illustrated in FIG. 3. The cam surfaces 46 are formed on an upper, inner portion of the lever 18 and are oriented for sliding engagement with the curved surface of the head 40. As the lever 18 is moved in an arc about the pivot pin 20 from the first location shown in FIG. 2 and to the second location illustrated in FIG. 3, the head 40 rides along the cam surfaces 46 and moves the plunger device 36 in a forward direction toward the cartridge 12 when the cartridge 12 is received in the receptacle 32 of the holder 26.

As is best shown in FIG. 3, a coiled compression spring 48 surrounds the shaft 38 of the plunger device 36 and is located between the head 40 and the facing opening of the channel 22 formed in the handle 16. When the lever 18 is released from the depressed position that is illustrated in FIG. 3, the spring 48 moves the plunger device 36 in a rearward direction. Rearward movement of the plunger device 36 causes the lever 18 in turn to swing about the pivot pin 20 from the second location shown in FIG. 3 and back to the first location shown in FIG. 2. When the plunger device 36 is in the position shown in FIG. 2, the front end of the plungers 42 is preferably located slightly behind the rear end of the cartridge 12 to allow the cartridge to be removed from the receptacle 32. However, other constructions are also possible (for example, the plunger device 36 may be somewhat longer such that the lever 18 must be moved to the orientation shown in FIG. 1 before the plunger device 36 clears the cartridge 12).

Figure 4:
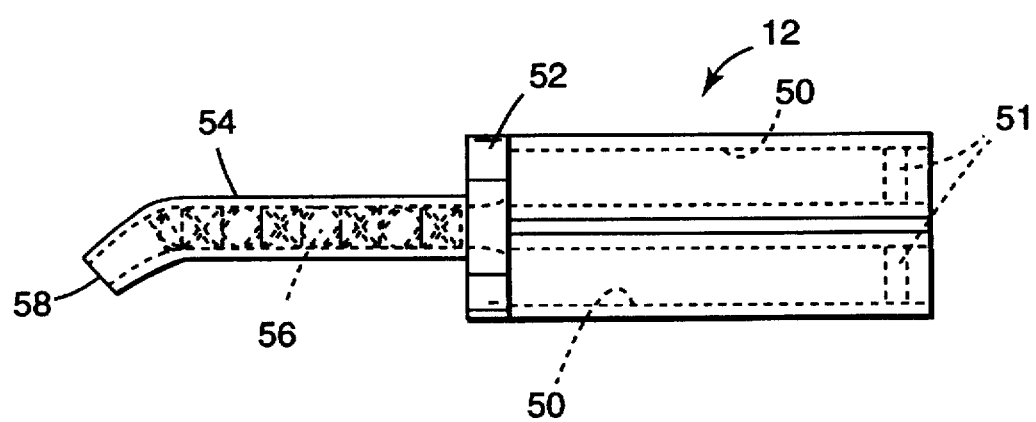
FIG. 4 is an enlarged side view in partial section of the dispensing cartridge alone that is illustrated in FIGS. 1–3.

Referring now to FIG. 4, the cartridge 12 is shown alone in more detail and includes a pair of elongated, side-by-side barrels that each contain one of the internal cylindrical chambers 50. The barrels are integrally joined together by an elongated web. Each of the chambers 50 is adapted to receive one component of a two-component material. Each chamber 50 also receives a sliding piston 51 that separates its component from the rear, open end of the respective chamber 50. The cartridge 12 also includes a housing 52 that is secured to the front ends of the barrels. The housing 52 includes an elongated, forwardly extending exit conduit 54 having an internal passageway. A rear end portion of the passageway includes a flared channel that communicates the passageway with front end portions of both chambers 50.

A static mixer 56 is received in the passageway of the exit conduit 54. The static mixer 56 includes a plurality of helical static mixing elements and is optionally secured to the exit conduit 54 by welding or other means. When the lever 18 is moved from the location shown in FIG. 2 and toward the location depicted in FIG. 3, the plungers 42 advance the pistons 51 of the cartridge 12. Preferably, once the lever 18 reaches the location shown in FIG. 3, the pistons 51 are touching at or very near the front end of the chambers 50 so that little, if any, of the components remain in the chambers 50. As a consequence, at least a majority and preferably substantially all of the components are expelled from the chambers 50 after a single stroke of the lever 18, a particular advantage when the cartridge 12 is intended for single patient use.

As the pistons 51 are advanced, the components are directed from the chambers 50 to the exit conduit 54. The static mixing elements successively divide, recombine and mix the components as they pass through the exit conduit 54 such that the components are thoroughly mixed once discharged from a front outlet 58 of the exit conduit 54. Suitable materials for the static mixer 56 include polypropylene (such as "PROFAX" brand, no. 6331NW; from Himont USA).

Preferably, the exit conduit 54 is curved along its length as shown in the drawings to facilitate application of the mixed components to a particular location. Optionally, the cartridge 12 is assembled by inserting the static mixer 56 in the exit conduit 54, and then connecting the barrels to the housing 52 by an adhesive, a welding process or other joining means. As another option, the barrels, the housing 52 and the static mixer 56 are made as two integral molded half sections that are joined together subsequent to molding.

Suitable materials for making the barrels, the housing 52 and the pistons of the cartridge 12 include amorphous polyolefins such as are sold under the trade name "ZEONEX" grade 480 (from Nippon Zeon Co., Ltd., Tokyo, Japan). Alternative materials include polyethylenes such as are sold under the trade name "ALATHON H5618" (from Occidental Chemical Corporation, Dallas, Tex.), and polypropylene resins such as are sold under the trade name "PROFAX", no. 6331NW; from Himont USA). Further information regarding suitable materials is contained in pending U.S. patent application Ser. No. 08/202,390 entitled "DELIVERY SYSTEM FOR WATER-CONTAINING DENTAL MATERIALS" filed on Feb. 28, 1994, the disclosure of which is expressly incorporated by reference herein.

Optionally, an elongated metal cannula is attached to the front of the exit conduit 54 and extends outwardly from the opening 58. The cannula is not shown in the drawings, but preferably has an outwardly flared rear section that is located in the exit conduit 54 rearwardly of the outlet 58 and forwardly of the front end of the static mixer 56. The flared rear section retains the cannula in coupled relation to the exit conduit 54. The flared rear section also enables the cannula to swivel about its longitudinal axis relative to the exit conduit 54 when desired. Furthermore, the cannula is preferably bendable as needed by finger pressure to a straight configuration or any one of a number of curved configurations to enhance application of the mixed material to a selected location.

As can be appreciated, the cylindrical portion of the shaft 38, the cylindrical channel 22 of the body 14 and the cylindrical rear extension 28 of the holder 26 provide a means for pivotally connecting the holder 26 and the pair of plungers 42 to the body 14. This pivotal connection enables the holder 26 and the plungers 42 to swivel in an arc that is designated by the numeral 60 in FIG. 2. The arc 60 extends in a reference plane that is perpendicular to the direction of advancement of the plungers 42 when the lever 18 is pivoted about the pivot pin 20 in a direction toward the handle 16.

As a consequence, the operator may conveniently select any one of a number of different orientations of the cartridge 12 relative to the applicator 10 in order to facilitate dispensing of material directly to a particular application site. When desired, the orientation of the cartridge 12 can be changed by simply grasping the flat sides 34 of the holder 26 and turning the same about arc 60 as needed. As the holder 26 is so moved, the plunger device 36 also turns simultaneously therewith so that the longitudinal axes of the plungers 42 remain aligned with the respective longitudinal axes of the chambers 50 of the cartridge 12 regardless of the ultimate rotational orientation of the latter.

Those skilled in the art may recognize that various additions and modifications may be made to the presently preferred embodiment that is described in detail above without departing from the spirit of the invention. For example, the rib 30 and groove 24 may be larger than as is shown in the drawings, and the extension 28 may be thicker and optionally extend the length of the channel 22. Furthermore, the rib 30 and groove 24 may be replaced with a threaded coupling, or with one or more non-removable, radially oriented pins that extend through the body 14 surrounding the channel 22 and into a groove formed on the extension 28. The channel 22 could also include a rear, stepped down portion equal in inner diameter to the inner diameter of the extension 28 to enhance support of the plunger device 36.

Moreover, while the rotatable cartridge 12 as described above is intended for single-patient use, a larger cartridge adapted for multiple uses with multiple patients is also possible for use in the medical or dental arena, or for use with multiple tasks in industrial, commercial or residential settings. A cartridge with more than two chambers may also be provided. Additionally, other types of drive means such as a pneumatic, electric or hand-ratchet drive mechanism may be employed in substitution for the drive means described above. Also, a conventional dual chamber cartridge having an enlarged rear flange may be used in place of the cartridge 12, and the holder 26 may be modified accordingly to grasp the rear flange of such cartridge.

As another alternative, a dual chamber cartridge may be provided with round front and rear flanges and received in a cylindrical receptacle of a holder, such that the cartridge along with the plunger device may be pivoted about the central axis of the cartridge (which coincides with the direction of advancement of the plunger device) while the holder remains stationary relative to the applicator body. A number of other variations are also possible. As a result, the invention should not be deemed limited to the specific embodiments that are set out in detail above, but only by a fair scope of the claims that follow along with their equivalents.

We claim:

1. An applicator assembly comprising a dual chamber cartridge having two chambers each with a longitudinal axis and an applicator for dispensing material from said dual chamber cartridge, said applicator including:

a body having a handle;

a holder for removably receiving said dual chamber cartridge;

a pair of elongated, side-by-side plungers each having a longitudinal axis; and drive means for advancing said pair of plungers in a certain direction toward said cartridge when received in said holder, said pair of plungers being pivotally connected to said body for selective movement in an arc about said certain direction, said holder pivotally connecting said cartridge to said body for selective movement in said arc in order to vary the rotative orientation of said cartridge relative to the handle, said longitudinal axes of said plungers being aligned with respective longitudinal axes of said chambers during a dispensing operation regardless of the rotational orientation of said cartridge.

2. The applicator of claim 1, wherein said applicator includes a shaft connected to said pair of plungers, and wherein said shaft has a cylindrical side wall in engagement with said body.

3. The applicator of claim 1, wherein said plungers are slidably connected to said body.

4. The applicator of claim 1, wherein said applicator includes a shaft connected to said plungers, wherein said shaft has a head remote from said plungers, wherein said drive means comprises a lever pivotally connected to said body, and wherein said lever includes a cam surface in engagement with said head.

5. An applicator for dispensing material from a dual chamber cartridge, said applicator comprising:

a body having a handle;

a holder for removably receiving a dual chamber cartridge;

a pair of elongated, side-by-side plungers: each having a longitudinal axis; and drive means for advancing said pair of plungers in a certain direction toward the cartridge when received in said holder, said pair of plungers being pivotally connected to said body for selective movement in an arc about said certain direction, said holder pivotally connecting the cartridge to said body for selective movement in said arc in order to vary the rotative orientation of the cartridge relative to the handle, wherein said holder is selectively movable in said arc in order to move said cartridge.

6. The applicator of claim 5, wherein said holder and said pair of plungers are connected together for simultaneous movement in said arc.

7. The applicator of claim 6, wherein said holder and said pair of plungers are detachably connected together.

8. The applicator of claim 5, wherein said body includes a cylindrical channel, and wherein said holder includes a rear cylindrical extension matingly received in said channel.

9. The applicator of claim 8, wherein one of said channel and said extension includes a rib, and wherein the other of said channel and said extension includes a groove that receives said rib, said rib and said groove being slidable to one another as said holder is moved in said arc.

10. An applicator assembly comprising:

applicator including a body having a handle, a lever pivotally connected to said body, and a pair of plungers shiftably coupled to said body, said lever being connected to said plungers for advancing said plungers relative to said body when said lever is moved a certain distance from a first location and to a second location relative to said handle, said applicator also including a receptacle; and a cartridge removably received in said receptacle and having a pair of side-by-side chambers, said cartridge including a pair of pistons received in said chambers and movable in said chambers over a limited path of travel, said plungers being in contact with said pistons for advancing said pistons when said lever is moved said certain distance, said chambers being of a size sufficiently small such that said pistons are moved a distance greater than one-half of their limited path of travel when said lever is moved said certain distance such that at least one-half of the contents of said chambers is displaced from said chambers, wherein said applicator includes a holder presenting said receptacle, and wherein said holder is pivotally connected to said body.

* * * * *